US00PP11643P

United States Patent [19]

Oudshoorn

[11] Patent Number: Plant 11,643

[45] Date of Patent: Nov. 21, 2000

[54] PEROVSKIA PLANT NAMED 'LITTLE SPIRE'

[75] Inventor: Herbert Oudshoorn, Rijpwetering, Netherlands

[73] Assignee: Future Plants V.O.F., Noordwijk, Netherlands

[21] Appl. No.: 09/213,445

[22] Filed: Dec. 17, 1998

[51] Int. Cl.[7] ..... A01H 5/00

[52] U.S. Cl. ..... Plt./263

[58] Field of Search ..... Plt./226, 263

*Primary Examiner*—Howard J. Locker
*Assistant Examiner*—Michelle Kizilkaya
*Attorney, Agent, or Firm*—C. A. Whealy

[57] ABSTRACT

A distinct cultivar of Perovskia plant named 'Little Spire', characterized by its upright and relatively compact plant habit; relatively short flower stems; small dark purple blue flowers; numerous flowers per plant; and excellent garden performance.

1 Drawing Sheet

BACKGROUND OF THE INVENTION

The present invention relates to a new and distinct cultivar of Perovskia plant, botanically known as *Perovskia hybrida*, and hereinafter referred to by the cultivar name Little Spire.

The new Perovskia was discovered by the Inventor in Rijpwetering, The Netherlands, in 1995 in a seed bed of sown *Perovskia hybrida* seed from various crosses of unidentified Perovskia seedling selections.

Asexual reproduction of the new cultivar by terminal cuttings taken at Rijpwetering, The Netherlands, has shown that the unique features of this new Perovskia are stable and reproduced true to type in successive generations.

SUMMARY OF THE INVENTION

Plants of the cultivar Little Spire have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Little Spire'. These characteristics in combination distinguish 'Little Spire' as a new and distinct cultivar:

1. Upright and relatively compact plant habit with relatively short flower stems.

2. Small dark purple blue flowers.

3. Freely flowering with numerous flowers per plant.

4. Excellent garden performance; good weather tolerance.

Plants of the cultivar Little Spire can be compared to plants of the nonpatented *Perovskia atriplicifolia* cultivar Blue Spire. However in side-by-side comparisons conducted in Rijpwetering, The Netherlands, plants of the cultivar Little Spire differ from plants of the cultivar Blue Spire in the following characteristics:

1. Plants of the new Perovskia are more compact than of plants of the cultivar Blue Spire.

2. Leaves of plants of the new Perovskia appear slightly grayer, are less deeply serrate and more acuminate than leaves of plants of the cultivar Blue Spire.

3. Plants of the new Perovskia have shorter flower stems than plants of the cultivar Blue Spire.

4. Plants of the new Perovskia have darker purple blue flower color than plants of the cultivar Blue Spire.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical plant of the new Perovskia in outdoor cultivation. Flower and foliage colors in the photograph may appear different than the actual colors due to light reflectance.

DETAILED BOTANICAL DESCRIPTION

In the following description, color references are made to The Royal Horticultural Society Colour Chart except where general terms of ordinary dictionary significance are used. Plants used for the description were grown in 1.5-liter containers under outdoor production conditions during the spring and summer which closely approximate commercial production conditions in Rijpwetering, The Netherlands.

Botanical classification: *Perovskia hybrida* cultivar Little Spire.

Parentage:

*Female parent*.—Unidentified *Perovskia hybrida* seedling selection.

*Male parent—Unidentified Perovskia hybrida* seedling selection.

Propagation:

*Type cutting*.—Terminal vegetative cuttings.

*Time to initiate and develop roots*.—About 14 days during the spring under outdoor production conditions.

*Rooting habit*.—Numerous and fine.

Plant description:

*Crop time*.—From cuttings, about 30 weeks are required to produce a fully-grown flowering plant in a 1.5-liter container.

*Form*.—Upright, narrow inverted triangle, herbaceous perennial herb. Appropriate for 1.5-cm containers.

*Branching habit*.—Basally branching, moderate.

*Plant height* (*from soil level to top of plant plane*).—About 65 cm.

*Area of spread*.—About 22.5 cm.

*Vigor*.—Moderate.

*Branches*.—Quantity: Typically 6 to 10. Length: About 40 cm. Diameter: About 2.75 mm. Internode length: About 2.75 cm. Shape: Square in cross-section.

Texture: Soft tomentose. Color: Light gray-green, 190C–190D.

*Foliage description*.—Leaves simple, generally symmetrical, opposite and long persisting. Quantity per lateral branch: Typically about 30. Length: About 4.25 cm. Width: About 1.2 cm. Aspect: Somewhat upright. Shape: Elliptic. Apex: Acute. Base: Acuminate. Margin: Serrate. Texture: Viscid, slightly pubescent. Color: Young foliage, upper surface: Dulled green, 138B. Young foliage, lower surface: 139C. Mature foliage, upper surface: Dulled green, 138B. Mature foliage, lower surface: 139C. Venation, upper surface: 138B. Venation, lower surface: 190C. Petiole: Length: About 1.25 mm. Diameter: About 1.25 mm. Color: Upper surface: Dulled green, 138B. Lower surface: Greyed-green, 190C.

Flower description:

*Flower type and habit*.—Small flowers in 6-flowered vertillicasters arranged in terminal racemes; sessile. Freely flowering. Flowers last about 6 days. Not persistent.

*Natural flowering season*.—Continuously flowering typically during August through September in the Northern Hemisphere.

*Quantity*.—Very freely flowering with about 50 flowers per raceme. One-year old plants will usually have about 1,000 to 1,500 flowers.

*Fragrance*.—Not discerned.

*Flower buds*.—Length: About 5.5 mm. Diameter: About 2.5 mm. Shape: Ovate. Rate of opening: About 5 weeks from visible bud to fully opened flower. Color: Dark blue, 103A, with violet, 88C–88D, hairs.

*Flower size*.—Diameter: About 4.5 mm. Depth (tube length): About 6 mm.

*Corolla*.—Shape: Bilabiate; tubular/campanulate; upper lip, 4-toothed; lower lip, entire. Petal length: About 1 cm. Petal width: Upper lip, about 5 mm; lower lip, about 3 mm. Petal apex: Rounded. Petal margin: Entire. Texture: Smooth to sparsely pubescent. Color: Petal, upper surface, when opening: Dark purple blue; upper lip, 93B; lower lip, 89B. Petal, lower surface, when opening: Violet, 93C. Petal, upper surface, opened flower: Dark purple blue; upper lip, 93B; lower lip, 89B. Petal color does not fade. Petal, lower surface, opened flower: Violet, 93C.

*Calyx*.—Shape: Tubular/campanulate; sepals, elliptic, fused at base. Length: About 5 mm. Diameter: About 2.5 mm. Sepal quantity: Five. Sepal apex: Rounded to acute. Sepal margin: Entire. Texture: Pubescent. Color: Dark blue, 103A, with violet, 88C–88D, hairs.

*Reproductive organs*.—Stamens: Stamen number: Four, only 2 fertile. Anther shape: Basifixed. Anther size: About 1 mm. Anther color: Dark blue. Pollen amount: Sparse. Pollen color: White. Pistils: Pistil length: About 1.3 cm. Stigma color: Pale violet blue to pale gray. Style length: About 1.1 cm. Style color: Pale violet blue. Ovary color: Dark green.

*Seed*.—Seed production has not been observed.

Weather tolerance: Plants of the new Perovskia have exhibited good tolerance to rain, wind and low temperatures; good garden performance.

Disease resistance: Under commercial conditions, resistance to diseases common to Perovskia has not been observed.

It is claimed:

1. A new and distinct cultivar of Perovskia plant named 'Little Spire', as illustrated and described.

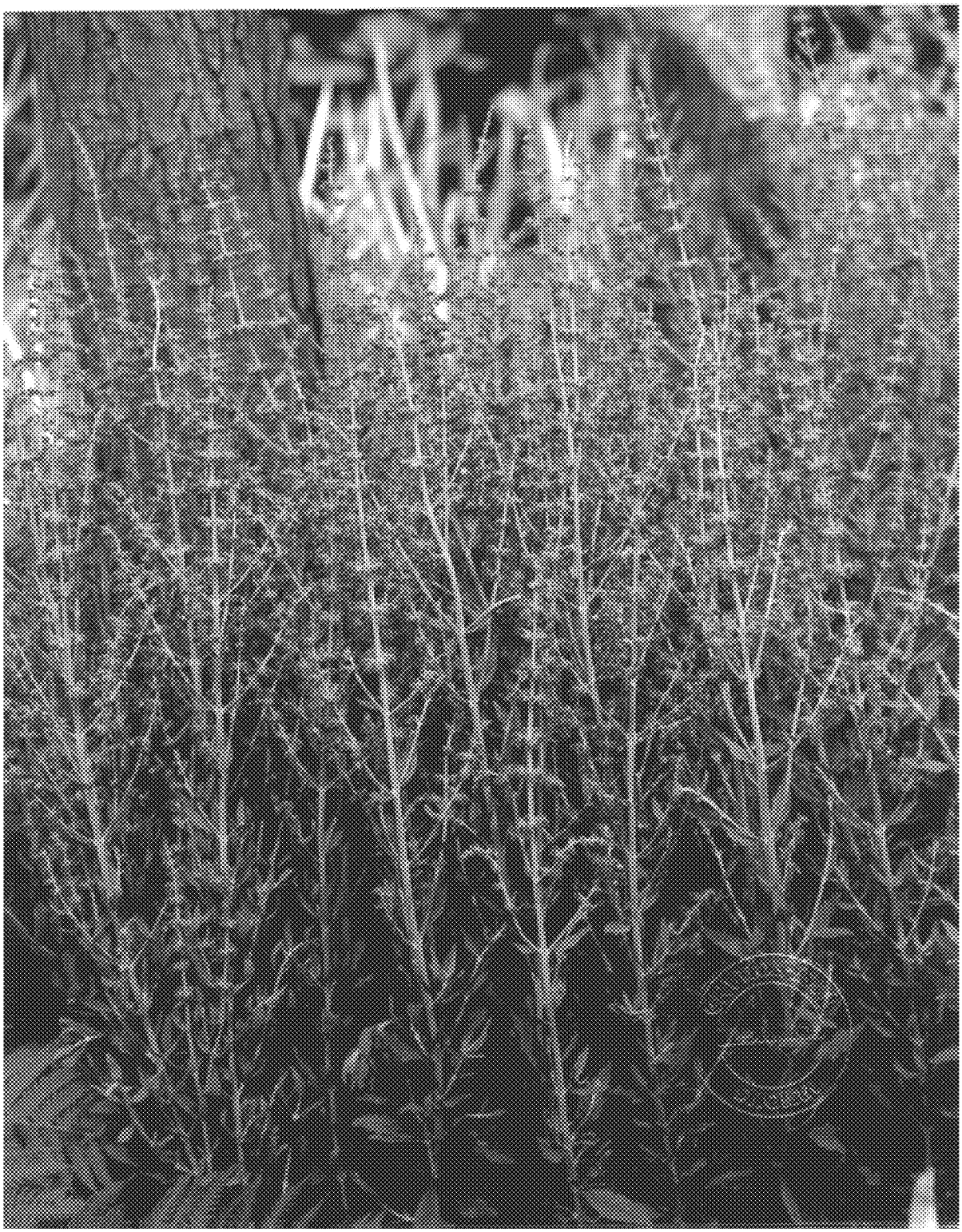

* * * * *